United States Patent
Sato et al.

(10) Patent No.: US 9,549,879 B2
(45) Date of Patent: Jan. 24, 2017

(54) POWDER-LIQUID DENTAL CURABLE MATERIAL KIT

(71) Applicant: Tokuyama Dental Corporation, Tokyo (JP)

(72) Inventors: Megumi Sato, Tokyo (JP); Kei Nakashima, Tokyo (JP); Koji Matsushige, Tokyo (JP)

(73) Assignee: TOKUYAMA DENTAL CORPORATION, Tokyo (JP)

( * ) Notice: Subject to any disclaimer, the term of this patent is extended or adjusted under 35 U.S.C. 154(b) by 124 days.

(21) Appl. No.: 14/383,347

(22) PCT Filed: Mar. 5, 2013

(86) PCT No.: PCT/JP2013/056013
§ 371 (c)(1),
(2) Date: Sep. 5, 2014

(87) PCT Pub. No.: WO2013/133280
PCT Pub. Date: Sep. 12, 2013

(65) Prior Publication Data
US 2015/0038614 A1    Feb. 5, 2015

(30) Foreign Application Priority Data

Mar. 9, 2012 (JP) ................................. 2012-052581

(51) Int. Cl.
*A61K 6/083* (2006.01)
*A61K 6/00* (2006.01)

(52) U.S. Cl.
CPC ............. *A61K 6/083* (2013.01); *A61K 6/0047* (2013.01)

(58) Field of Classification Search
CPC .................................................. A61K 6/0047
See application file for complete search history.

(56) References Cited

U.S. PATENT DOCUMENTS

| | | | |
|---|---|---|---|
| 4,616,073 A * | 10/1986 | Antonucci | A61K 6/083 433/212.1 |
| 4,880,887 A | 11/1989 | Hasegawa | |
| 4,946,901 A | 8/1990 | Gasser | |
| 5,407,973 A | 4/1995 | Hasegawa et al. | |
| 6,852,775 B1 | 2/2005 | Soglowek | |
| 2002/0058727 A1* | 5/2002 | Nakayama | C08F 265/06 523/120 |
| 2004/0068041 A1 | 4/2004 | Nakayama et al. | |

FOREIGN PATENT DOCUMENTS

| | | |
|---|---|---|
| JP | 63-216811 | 9/1988 |
| JP | 6-219919 | 8/1994 |
| JP | 09-067222 | 3/1997 |
| JP | 11-071220 | 3/1999 |
| JP | 11-228330 | 8/1999 |
| JP | 2003-105008 | 4/2003 |
| JP | 2005-255654 | 9/2005 |
| JP | 2006183013 A2 | 7/2006 |
| JP | 2012-140386 | 7/2012 |
| JP | 2013-035780 | 2/2013 |

OTHER PUBLICATIONS

Extended European Search Report dated Sep. 9, 2015 issued in the corresponding European patent application No. 13757521.3.
International Search Report dated Apr. 9, 2013 filed in PCT/JP2013/056013.

* cited by examiner

*Primary Examiner* — Michael Pepitone
(74) *Attorney, Agent, or Firm* — Rankin, Hill & Clark LLP

(57) ABSTRACT

A powder-liquid dental curable material kit composed of (A) a liquid material and (B) a powder material, wherein the liquid material (A) contains (a1) a radically polymerizable (meth)acrylic monomer, (a2) an organic halogen compound and (a3) a radical chain transfer agent; the powder material (B) contains (b1) non-crosslinked resin particles, (b2) a pyrimidinetrione compound and (b3) an organic metal compound; and (Z) a peroxide is blended in at least one of the liquid material (A) and the powder material (B). This curable material kit is capable of reducing the heat generation during the curing of a curable material which is a mixture of the liquid material (A) and the powder material (B) and is not susceptible to the excessive prolongation of the curing time even when the curable material is cured by a brush-on technique, thereby ensuring an appropriate curing time for both of a brush-on technique and a kneading technique.

11 Claims, 1 Drawing Sheet

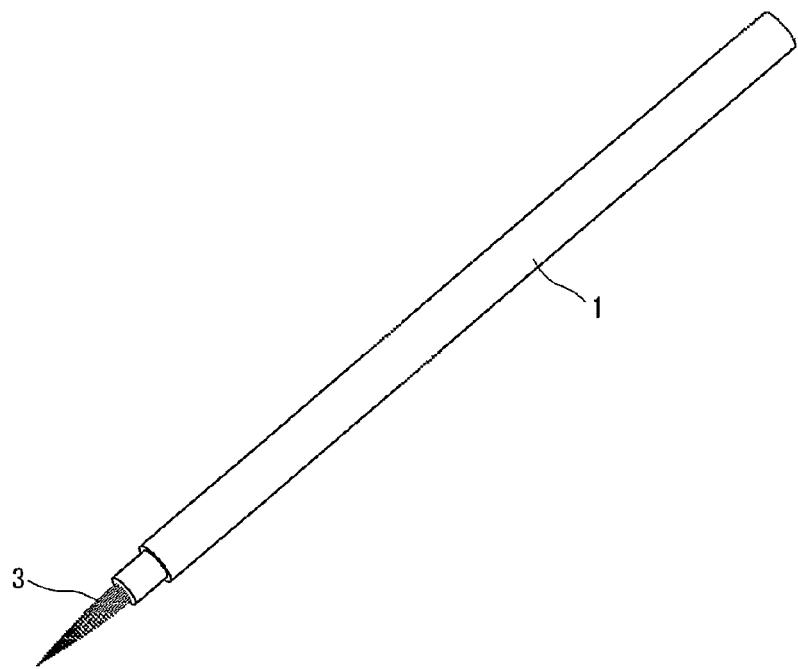

POWDER-LIQUID DENTAL CURABLE MATERIAL KIT

CROSS-REFERENCE TO RELATED APPLICATIONS

This application is a National Phase Application of International Application No. PCT/JP2013/056013, filed Mar. 5, 2013, which claims the priority of Japan Patent Application No. 2012-052581, filed Mar. 9, 2012. The present application claims priority from both applications and each of these applications is herein incorporated in their entirety by reference.

TECHNICAL FIELD

The present invention relates to a powder-liquid dental curable material kit composed of a liquid material and a powder material both of which are mixed together to be used for dental applications.

BACKGROUND ART

A powder-liquid curable material kit used in the field of dental treatment is composed of a liquid material containing a radically polymerizable (meth)acrylic monomer such as a lower alkyl(meth)acrylate-based monomer as the main component and a powder material containing a non-crosslinked resin such as polymethyl methacrylate as the main component, and a curable material is prepared by mixing together the powder material and the liquid material.

In this curable material kit, a chemical polymerization type radical polymerization initiator composed of a plurality of constituent components is used to polymerize the above radically polymerizable (meth)acrylic monomer. That is, the constituent components of this chemical polymerization type polymerization initiator are separately blended in the liquid material and the powder material so that a radical is produced when the liquid material and the powder material are mixed together to initiate the radical polymerization of the above (meth)acrylate-based monomer.

Although this chemical polymerization type radical polymerization initiator is generally a combination of an organic peroxide and an aromatic tertiary amine, a combination of a pyrimidinetrione derivative, an organic metal compound and an organic halogen compound is also known as an advantageous polymerization initiator because the discoloration of a cured product hardly occurs (refer to Patent Documents 1 and 2).

Since a cured product obtained by radical polymerization contains the non-crosslinked resin, it has the advantage of high toughness as compared with a cured product containing an inorganic filler. Therefore, the powder-liquid dental curable material kit is very useful for dental clinical applications where high toughness is required and commercialized as an adhesive resin cement material which is used for the splinting of a mobile tooth, the bonding and baoding of an orthodontic and the bonding of an artificial tooth and as a normal-temperature polymerization resin material which is used for the repair of a broken denture.

In most of these applications, a mixture of the liquid material and the powder material is often cured in the oral cavity of a patient. In this case, the amount of heat generated during curing must be small in order not to hurt the patient. Further, it is also important to control the time (curing time) elapsed until the mixture is cured according to the clinical situation.

In the above powder-liquid dental curable material kit, a technology for controlling the curing time by slowing down the curing rate moderately by using a polymerization inhibitor has been proposed in order to control the heating temperature and the curing time (refer to Patent Document 3). However, when the curing time is controlled by this method, a polymerization reaction proceeds at once after the polymerization inhibitor is used up to delay curing and disappears. Therefore, the technology is ineffective for the suppression of heat generation during curing.

Also, a technology for controlling the curing time arbitrarily and suppressing heat generation during curing without deteriorating the physical properties of a cured product by using a radical chain transfer agent has been reported (refer to Patent Document 4).

PRIOR ART DOCUMENTS

Patent Document 1: JP-A 63-216811
Patent Document 2: JP-A 11-228330
Patent Document 3: JP-A 9-67222
Patent Document 4: JP-A 11-071220

DISCLOSURE OF THE INVENTION

Problem to be Solved by the Invention

Techniques for curing a curable material composed of a powder material and a liquid material in a powder-liquid dental curable material kit are roughly divided into a kneading technique and a brush-on technique. They are used properly each time according to the clinical situation and the trial of an operator.

For example, the kneading technique is used to prepare resin sludge which is a curable material by injecting a powder material and a liquid material into a container such as a rubber cup and kneading them together by means of a spatula and generally employed to form a relatively large part such as a temporary crown (TEK) or a bridge.

Meanwhile, the brush-on technique is used to prepare resin sludge which is a curable material by impregnating a liquid absorbing material 3 (for example, a writing brush or a pencil brush) attached to the end of a stick 1 shown in FIG. 1 with a liquid material, applying the liquid absorbing material 3 to a powder material in this state, and compatibilizing the liquid material oozing out from the liquid absorbing material 3 with the adhered powder material. This technique is used for work on a fine site such as the control of a TEK inner wall or the repair of a denture base.

The above liquid absorbing material 3 is called "brush" in Japan.

Accordingly, the powder-liquid curable material kit which includes the aforementioned chemical polymerization type radical polymerization initiator has a problem that the rate of curing with the brush-on technique is too slow as compared with that of the kneading technique. That is, since the mixing of the liquid material and the powder material is carried out by the penetration of the liquid material oozing out from the liquid absorbing material 3 into the powder material in the brush-on technique, it is presumed that oxygen required for a polymerization reaction tends to run short during curing as compared with the kneading technique in which these materials are forcedly stirred, thereby significantly prolonging the curing time.

Therefore, in the powder-liquid curable material, when the curing time is controlled by adding the radical chain transfer agent as proposed in Patent Document 4, the curing time which can be satisfactory for both the kneading technique and the brush-on technique cannot be ensured. That is, since the kneading technique and the brush-on technique differ from each other in curing behavior, when the curing time is controlled to a preferred range for one of the techniques, it becomes inappropriate for the other technique, thereby causing a problem that operability for curing deteriorates.

For example, in the case of the kneading technique, the obtained resin sludge (curable material) is built up on a relatively large site to adjust its form. Therefore, quick curing is desired and the optimum curing time from the mixing of the powder material and the liquid material is approximately 1 minute 30 seconds to 3 minutes. Meanwhile, in the case of the brush-on technique, the obtained resin sludge is supplied to the repair work of a fine part and may be used in the oral cavity. Therefore, the optimum curing time is slightly longer than that of the kneading technique and approximately 3 to 4 minutes from the compatibilization of the liquid material oozing out from the liquid absorbing material 3 with the powder material.

However, even when the curing time is adjusted to a value suitable for the kneading technique by adding the radical chain transfer agent and the brush-on technique is used for curing, the curing time becomes much longer than the curing time suitable for the brush-on technique. When the curing time is adjusted to a value suitable for the brush-on technique, the curing time becomes too short in the kneading technique.

As understood from the above explanation, a dedicated kit including a powder material and a liquid material must be prepared for each technique for preparing resin sludge, thereby imposing a great burden on an operator. Thus, the improvement of this is strongly desired.

It is therefore an object of the present invention to provide a powder-liquid curable material kit used for dental applications which is composed of a liquid material and a powder material, wherein the kit is capable of reducing the heat generation during the curing of a curable material which is a mixture of the liquid material and the powder material and is not susceptible to the excessive prolongation of the curing time even when the curable material is cured by a brush-on technique, thereby ensuring an appropriate curing time for both of a brush-on technique and a kneading technique.

Means for Solving the Problem

The inventors of the present invention conducted intensive studies to solve the above technical problem and found that the above problem can be solved by further blending a peroxide in a powder-liquid dental curable material kit which includes a chemical polymerization type radical polymerization initiator composed of a pyrimidinetrione compound, an organic metal compound and an organic halogen compound and a radical chain transfer agent. The present invention was accomplished based on this finding.

According to the present invention, there is provided a powder-liquid dental curable material kit composed of a liquid material (A) and a powder material (B), and including a combination of an organic halogen compound, a pyrimidinetrione compound and an organic metal compound as a radical polymerization initiator, wherein
the liquid material (A) contains a radically polymerizable (meth)acrylic monomer (a1), the organic halogen compound (a2) and a radical chain transfer agent (a3); the powder material (B) contains non-crosslinked resin particles (b1), a pyrimidinetrione compound (b2) and the organic metal compound (b3); and a peroxide (Z) is blended in at least one of the liquid material (A) and the powder material (B).

In the powder-liquid dental curable material kit of the present invention, preferably,
(1) the liquid material (A) contains 0.001 to 5 parts by mass of the organic halogen compound (a2) and 0.01 to 10 parts by mass of the radical chain transfer agent (a3) based on 100 parts by mass of the radically polymerizable monomer (a1), and the powder material (B) contains 0.03 to 5 parts by mass of the pyrimidinetrione compound (b2) and 0.0003 to 0.02 part by mass of the organic metal compound (b3) based on 100 parts by mass of the resin particles (b1);
(2) the peroxide (Z) is blended in the powder material (B) in an amount of 0.03 to 5 parts by mass based on 100 parts by mass of the resin particles (b1);
(3) the organic halogen compound (a2) is a quaternary ammonium halide;
(4) the radical chain transfer agent (a3) is a mercaptan, halogenated hydrocarbon or phenyl group-containing monoolefin;
(5) the non-crosslinked resin particles (b1) are (meth)acrylate resin particles;
(6) the pyrimidinetrione compound is a compound represented by the following general formula (1):

[chemical formula 1]

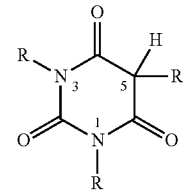

wherein three R's are each independently a hydrogen atom, alkyl group having 1 to 8 carbon atoms, cycloalkyl group having 3 to 8 carbon atoms or phenyl group, with the proviso that all of them cannot be hydrogen atoms;
(7) the organic metal compound (b3) is a copper or iron compound; and
(8) the organic metal compound (b3) is at least one selected from the group consisting of acetylacetone copper (II), copper acetate (II), copper oleate (II) and acetylacetone iron (II).

Effect of the Invention

Since a combination of the organic halogen compound (a2), the pyrimidinetrione compound (b2) and the organic metal compound (b3) is used as the radical polymerization initiator and the radical chain transfer agent (a3) is used in the powder-liquid dental curable material kit of the present invention, heat generation during curing is suppressed and the curing rate can be slowed down and controlled according to the clinical situation. Further, since the peroxide (Z) is further used in addition to these, the excessive prolongation of the curing time when the liquid material (A) and the powder material (B) are mixed together by the brush-on technique is suppressed. That is, inconvenience that the curing time of the brush-on technique becomes too long as compared with the curing time of the kneading technique is avoided effectively, and the prolongation of the curing time in the brush-on technique is kept at a value slightly larger than that of the kneading technique.

As understood from this, the powder-liquid dental curable material kit of the present invention exhibits completely different behavior from that of the prior art when the brush-on technique is employed, whereby even when it is used for any one of these techniques as a shared kit for both of the brush-on technique and the kneading technique, there is no big difference in the prolongation of the curing time between them. Therefore, the kit of the present invention can be clinically advantageously used as a material which ensures high operability for both of the techniques.

In the present invention, the inventors of the present invention presume that the reason that the excessive prolongation of the curing time in the brush-on technique can be prevented is as follows.

As already stated above, the reason why the curing rate is slow and the curing time is long in the brush-on technique is presumed as follows. That is, since the mixing of the liquid material and the powder material is carried out by the penetration of the liquid material oozing out from the aforementioned absorbing material 3 of FIG. 1 into the powder material in this technique, oxygen required for a polymerization reaction runs short during curing as compared with the kneading technique in which these materials are forcedly stirred.

Therefore, according to the present invention, the peroxide becomes an oxygen supply source, thereby eliminating a shortage of oxygen during curing in the brush-on technique with the result that the excessive prolongation of the curing time is suppressed.

BRIEF DESCRIPTION OF THE DRAWINGS

FIG. 1 This is a diagram of a jig used for the brush-on technique.

BEST MODE FOR CARRYING OUT THE INVENTION

The dental curable material kit of the present invention is composed of a liquid material (A) and a powder material (B), a combination of an organic halogen compound, a pyrimidinetrione compound and an organic metal compound is used as a radical polymerization initiator, these radical polymerization initiator components are separately blended in the liquid material (A) and the powder material (B), and further a peroxide is blended in the liquid material (A) and/or the powder material (B), preferably the liquid material (A).

<Liquid Material (A)>

The liquid material (A) contains a radically polymerizable (meth)acrylic monomer (a1), an organic halogen compound (a2) which is a radical polymerization initiator component and a radical chain transfer agent (a3) as essential components, and preferably further a peroxide (Z).

1. Radically Polymerizable (Meth)Acrylic Monomer (a1);

In the present invention, the liquid material (A) contains a radically polymerizable (meth)acrylic monomer as the main component. This radically polymerizable monomer is generally used in the dental field from the viewpoint of high polymerizability and adaptability to a human body.

Examples of the radically polymerizable (meth)acrylic monomer include, but are not limited to, the following monomers.

methyl(meth)acrylate, ethyl(meth)acrylate, isopropyl (meth)acrylate, 2-hydroxyethyl(meth)acrylate, tetrahydrofurfuryl(meth)acrylate, glycidyl(meth)acrylate, 2-(meth)acryloxyethyl propionate, ethylene glycol di(meth)acrylate, diethylene glycol di(meth)acrylate, triethylene glycol di(meth)acrylate, butylene glycol di(meth)acrylate, neopentyl glycol di(meth)acrylate, 1,3-butanediol di(meth)acrylate, 1,4-butanediol di(meth)acrylate, 1,6-hexanediol di(meth)acrylate, 2,2-bis ((meth)acryloxyphenyl)propane, 2,2-bis[4-(2-hydroxy-3-(meth)acryloxyphenyl)]propane, 2,2-bis(4-(meth) acryloxyethoxyphenyl)propane, 2,2-bis(4-(meth) acryloxydiethoxyphenyl)propane, 2,2-bis(4-(meth) acryloxypropoxyphenyl)propane, trimethylolpropane tri(meth)acrylate, pentaerythritol tri(meth)acrylate, trimethylolmethane tri(meth)acrylate, pentaerythritol tetra(meth)acrylate, dimethylaminoethyl(meth)acrylate, diethylaminoethyl(meth)acrylate and quaternary dimethylaminoethyl(meth)acrylate.

The above radically polymerizable(meth)acrylic monomers may be used alone or in combination of two or more.

In the present invention, out of these, lower alkyl(meth)acrylate-based monomers (especially alkyls having 4 or less carbon atoms bonded to the oxygen atoms of a carboxyl) are preferred and methyl methacrylate is particularly preferred since the operability of the obtained powder-liquid dental curable material is high and the cured product has such high toughness that it is hardly bent. For example, it is most preferred that methyl methacrylate should account for 50 wt % or more of the radically polymerizable (meth)acrylic monomer (a1).

2. Organic Halogen Compound (a2);

The organic halogen compound contained in the liquid material (A) is a component which serves as a polymerization initiator (may be referred to as "pyrimidinetrione-based initiator" hereinafter) when it is used in combination with the pyrimidinetrione compound (b2) and the organic metal compound (b3) which will be described hereinafter. Stated more specifically, a compound which forms a halide ion in the liquid material (A) is used.

The organic halogen compound used in this pyrimidinetrione-based initiator is typically a quaternary ammonium halide as exemplified by the following compounds.

dilauryl dimethyl ammonium chloride, lauryl dimethyl benzyl ammonium chloride, benzyl trimethyl ammonium chloride, diisobutylamine hydrochloride, tetra-n-butylammonium chloride, triethylamine hydrochloride, trimethylamine hydrochloride, dimethylamine hydrochloride, diethylamine hydrochloride, methylamine hydrochloride, ethylamine hydrochloride, isobutylamine hydrochloride, triethanolamine hydrochloride, β-phenylethylamine hydrochloride, acetylcholine chloride, 2-chlorotrimethylamine hydrochloride, (2-chloroethyl)triethylammonium chloride, tetra-decyl dimethyl benzyl ammonium chloride, tetraethylammonium chloride, tetramethylammonium chloride, trioctylmethylammonium chloride, benzyl dimethyl cetyl ammonium chloride, benzyl dimethyl stearyl ammonium chloride, dilauryl dimethyl ammonium bromide, tetrabutyl ammonium bromide and benzyl triethyl ammonium bromide.

These organic halogen compounds may be used alone or in combination of two or more.

In the present invention, dilauryl dimethyl ammonium chloride is particularly preferably used since especially high polymerization activity can be obtained.

The aforementioned organic halogen compound (a2) is used in an amount of 0.001 to 5 parts by mass, particularly 0.01 to 2 parts by mass based on 100 parts by mass of the aforementioned radically polymerizable (meth)acrylic monomer (a1). When the amount of this compound is small, the polymerization initiation properties of the pyrimidinetrione-based initiator are not exhibited fully, whereby a polymerization reaction does not proceed to the fullest extent and the physical properties of the cured product tend to greatly deteriorate. When the amount is larger than required, it may cause the coloration or discoloration of the cured product.

3. Radical Chain Transfer Agent (a3);

The radical chain transfer agent (a3) is used to receive a radical from a growing polymer chain so as to cause a chain transfer reaction. As proposed in the prior art, the polymerization rate is slowed down by using the radical chain transfer agent, thereby making it possible to secure a clinical work time.

The radical chain transfer agent is typically a mercaptan, halogenated hydrocarbon or phenyl-containing mono-olefin. Examples thereof include, but are not limited to, the following.

mercaptans:
    octyl mercaptan, lauryl mercaptan, t-dodecyl mercaptan, n-hexadecyl mercaptan, n-tetradecyl mercaptan, m-thiocresol, thiophenol, thioglycol (2-mercaptoethanol), 2-ethylhexyl thioglycolate and β-naphthalene thiol.

halogenated hydrocarbons:
    carbon tetrachloride and ethylene bromide.

phenyl group-containing mono-olefins:
    2-phenyl-1-propene(α-methylstyrene), 2-phenyl-1-butene, 2,4-diphenyl-4-methyl-1-pentene(α-methylstyrene dimer), 3,5-diphenyl-5-methyl-2-heptene, 2,4,6-triphenyl-4,6-dimethyl-1-heptene, 3,5,7-triphenyl-5-ethyl-7-methyl-2-nonene, 1,3-diphenyl-1-butene, 2,4-diphenyl-4-methyl-2-pentene, 3,5-diphenyl-5-methyl-3-heptene, 1,1-diphenylethylene, 2,4-diphenyl-4-methyl-1-pentene, 2-phenyl-1-propene and 1,3-diphenyl-1-butene.

These radical chain transfer agents (a3) may be used alone or in combination of two or more.

In the present invention, out of the above radical chain transfer agents (a3), phenyl group-containing mono-olefins are preferred, and 2,4-diphenyl-4-methyl-1-pentene (α-methylstyrene dimer) is most preferred as it is easily acquired.

The aforementioned radical chain transfer agent (a3) is used in an amount of preferably 0.01 to 10 parts by mass, particularly preferably 0.03 to 7 parts by mass, most preferably 0.05 to 5 parts by mass based on 100 parts by mass of the radically polymerizable (meth)acrylic monomer (a1). When this amount is small, curing heat generation is hardly suppressed and the effect of controlling the curing time tends to be hardly seen. When this amount is larger than required, curing is slowed down more than required and the physical properties of the obtained cured product tend to deteriorate.

4. Other Components:

In the present invention, other compounding agents except for the above components (a1) to (a3) may be added to the liquid material (A). Particularly, the peroxide (Z) which will be described hereinafter may be blended in this liquid material (A).

Other compounding agents except for the peroxide (Z) include an organic solvent such as ethanol, a polymerization inhibitor such as butyl hydroxy toluene or methoxy hydroquinone, an ultraviolet absorber such as 2-(2-benzotriazol)-p-cresol, a dye, a pigment, a perfume and an aromatic amine for improving the oxygen supply capacity of the peroxide. These compounding agents may be used in an amount which does not adversely affect the curing rate (curing time) and clinical work efficiency.

<Powder Material (B)>

The powder material (B) is mixed with the aforementioned liquid material (A) before use and contains non-crosslinked resin particles (b1), a pyrimidinetrione compound (b2) and an organic metal compound (b3) as essential components.

1. Non-Crosslinked Resin Particles (b1);

The non-crosslinked resin particles (b1) are a granular product of a resin (resin obtained from a monofunctional monomer) having substantially no crosslinked structure and a known material in this field. That is, since they have substantially no crosslinked structure, they dissolve in the aforementioned radically polymerizable (meth)acrylic monomer (a1) or swell in volume when they are immersed in the monomer.

When these non-crosslinked resin particles (b1) are mixed with the liquid material (A), they increase the viscosity of the obtained mixture (curable material), promote the polymerizability of the radically polymerizable monomer (a1) contained in the liquid material (A) and enhance the toughness of the obtained cured product.

Although non-crosslinked resin particles having such a low molecular weight that they have swellability with the radically polymerizable monomer (a1) may be used as the non-crosslinked resin particles (b1), resin particles which are dissolved in an amount of 10 parts or more by mass when 200 parts by mass of the resin particles (b1) are mixed with 100 parts by mass of the 23° C. radically polymerizable monomer (a1) and stirred are preferably used.

The non-crosslinked resin constituting the particles (b1) is not limited as long as it has the above swellability or solubility. Although a known synthetic resin or natural resin may be used, a resin having a refractive index of 1.4 to 1.7 which is useful as a dental filler is preferred.

Preferred examples of the above resin include the following resins.
    (meth)acrylate resins such as polymethyl methacrylate, polymers of an alkyl(meth)acrylate monomer having an alkyl chain with 4 or less carbon atoms (such as polyethyl methacrylate) and a copolymer of methyl methacrylate and ethyl methacrylate; polyolefin resins such as polyethylene and polypropylene; polyamides; polyesters; and polystyrenes.

In the present invention, (meth)acrylate resins are particularly preferred because the obtained cured products have high toughness.

Although the particle sizes of the aforementioned non-crosslinked resin particles (b1) are not particularly limited, the particles preferably have an average particle diameter of 200 μm or less from the viewpoint of compatibility with the radically polymerizable monomer (a1), and particularly preferably have an average particle diameter of 1 to 100 μm from the viewpoint of the permeability of the liquid material (A) in the brush-on technique.

The particle shape is not particularly limited and may be spherical, irregular or amorphous.

In the present invention, the non-crosslinked resin particles (b1) are preferably existent in the mixture (curable material) in an amount of 30 to 400 parts by mass, particularly 100 to 300 parts by mass based on 100 parts by mass of the polymerizable monomer (a1) when the liquid material (A) and the powder material (B) are mixed together from the viewpoints of the effect of promoting the polymerizability of the radically polymerizable (meth)acrylic monomer (a1) and the high toughness of the obtained cured product. That is, the mixing ratio of the liquid material (A) and the powder material (B) is set to ensure that the amount of the non-crosslinked resin particles (b1) based on the polymerizable monomer (a1) falls within the above range.

2. Pyrimidinetrione Compound (b2);

The pyrimidinetrione compound (b2) contained in the powder material (B) is a component which serves as a radical polymerization initiator when it is used in combination with the organic halogen compound (a2) contained in the liquid material (A) and the organic metal compound (b3) which will be described hereinafter. That is, the hydrogen atom of the pyrimidinetrione compound (b2) is withdrawn by the organic metal compound (b3) which will be described hereinafter to produce radical species. Further, the radical species react with oxygen in the air by the catalytic function of the organic halogen compound (a2) with the result that radical species having oxygen bonded to the 5-position carbon of the pyrimidinetrione compound (b2) are produced. The radical polymerization of the radically polymerizable (meth)acrylic monomer proceeds with the two radical species produced from the pyrimidinetrione compound as the starting points.

This pyrimidinetrione compound (b2) is known per se and represented by the following general formula (1):

[chemical formula 2]

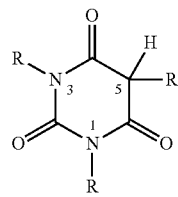

(1)

wherein three R's are each independently a hydrogen atom, alkyl group having 1 to 8 carbon atoms, cycloalkyl group having 3 to 8 carbon atoms or phenyl group, with the proviso that all of them cannot be hydrogen atoms.

Examples of the above alkyl group having 1 to 8 carbon atoms include methyl group, ethyl group, n-propyl group, iso-propyl group, n-butyl group, iso-butyl group, sec-butyl group, tert-butyl group, pentyl group, hexyl group, heptyl group and octyl group. Examples of the cycloalkyl group having 3 to 8 carbon atoms include cyclopropyl group, cyclobutyl group, cyclopentyl group, cyclohexyl group and 3- or 4-methylcyclohexyl group.

That is, in the above general formula (1), the 5-position hydrogen atom activated by a carbonyl group is withdrawn to become a radical starting point.

In the present invention, examples of the pyrimidinetrione compound include, but are not limited to, the following compounds which may be used alone or in combination of two or more.

5-methyl pyrimidinetrione, 5-ethyl pyrimidinetrione, 5-propyl pyrimidinetrione, 5-butyl pyrimidinetrione, 5-isobutyl pyrimidinetrione, 1,5-dimethyl pyrimidinetrione, 1,5-diethyl pyrimidinetrione, 1-methyl-5-ethyl pyrimidinetrione, 1-ethyl-5-methyl pyrimidinetrione, 1-methyl-5-butyl pyrimidinetrione, 1-ethyl-5-butyl pyrimidinetrione, 1-methyl-5-isobutyl pyrimidinetrione, 1-ethyl-5-isobutyl pyrimidinetrione, 1-methyl-5-cyclohexyl pyrimidinetrione, 1-ethyl-5-cyclohexyl pyrimidinetrione, 1-benzyl-5-phenyl pyrimidinetrione, 1,3,5-trimethyl pyrimidinetrione, 1,3-dimethyl-5-ethyl pyrimidinetrione, 1,3-dimethyl-5-butyl pyrimidinetrione, 1,3-dimethyl-5-isobutyl pyrimidinetrione, 1,3,5-triethyl pyrimidinetrione, 1,3-diethyl-5-methyl pyrimidinetrione, 1,3-diethyl-5-butyl pyrimidinetrione, 1,3-diethyl-5-isobutyl pyrimidinetrione, 1,3-dimethyl-5-phenyl pyrimidinetrione, 1,3-diethyl-5-phenyl pyrimidinetrione, 1-ethyl-3-methyl-5-butyl pyrimidinetrione, 1-ethyl-3-methyl-5-isobutyl pyrimidinetrione, 1-methyl-3-propyl-5-ethyl pyrimidinetrione, 1-ethyl-3-propyl-5-methyl pyrimidinetrione, 1-cyclohexyl-5-methyl pyrimidinetrione, 1-cyclohexyl-5-ethyl pyrimidinetrione, 5-butyl-1-cyclohexyl pyrimidinetrione, 5-sec-butyl-1-cyclohexyl pyrimidinetrione, 1-cyclohexyl-5-hexyl pyrimidinetrione, 1-cyclohexyl-5-octyl pyrimidinetrione and 1,5-dicyclohexyl pyrimidinetrione.

In the present invention, out of the above pyrimidinetriones, compounds obtained by substituting hydrogen bonded to a nitrogen atom by an alkyl group (preferably having 1 to 4 carbon atoms) or cycloalkyl group (preferably having 3 to 6 carbon atoms) are preferred from the viewpoints of solubility in the polymerizable monomer (a1) and radical polymerization activity, and the following compounds obtained by substituting hydrogen bonded to the nitrogen atom by a cycloalkyl group are most preferred.

1-cyclohexyl-5-methyl pyrimidinetrione, 1-cyclohexyl-5-ethyl pyrimidinetrione, 5-butyl-1-cyclohexyl pyrimidinetrione, 5-sec-butyl-1-cyclohexyl pyrimidinetrione, 1-cyclohexyl-5-hexyl pyrimidinetrione, 1-cyclohexyl-5-octyl pyrimidinetrione and 1,5-dicyclohexyl pyrimidinetrione.

When the powder material (B) is mixed with the liquid material (A), the above pyrimidinetrione is existent in the mixture in an amount of preferably 0.01 to 10 parts by mass, particularly preferably 0.05 to 7 parts by mass, most preferably 0.1 to 5 parts by mass based on 100 parts by mass of the radically polymerizable (meth)acrylic monomer (a1) in order to develop high polymerization activity.

Therefore, from this point of view, the amount of the pyrimidinetrione compound (b2) contained in the powder material (B) is preferably 0.03 to 5 parts by mass, particularly preferably 0.05 to 3 parts by mass based on 100 parts by mass of the non-crosslinked resin particles (b1). That is, if the amount of the pyrimidinetrione compound (b2) contained in the powder material (B) is set to the above range, when the liquid material (A) and the powder material (B) are mixed together to ensure that the amount of the non-crosslinked resin particles (b1) based on the radically polymerizable (meth)acrylic monomer (a1) falls within the above predetermined range, the amount of the pyrimidinetrione compound (b2) contained in the mixture can be set to the above range.

3. Organic Metal Compound (b3);

The organic metal compound (b3) contained in the powder material (B) is a component which serves as a polymerization initiator when it is used in combination with the organic halogen compound (a2) and the pyrimidinetrione compound (b2) as stated repeatedly. That is, the hydrogen atom of the pyrimidinetrione compound (b2) is withdrawn by this organic metal compound to produce radical species which react with oxygen in the air by the catalytic function of the aforementioned organic halogen compound (a2) to produce radical species having oxygen bonded to the 5-position carbon of the pyrimidinetrione compound (b2). The radical polymerization of the radically polymerizable (meth) acrylic monomer (a1) proceeds with these radicals as the starting points.

A conventionally known organic metal compound which is used in this type of initiator may be used as the organic metal compound (b3). Examples thereof include, but are not limited to, the following compounds which may be used alone or in combination of two or more.

Copper Compounds:
    acetylacetone copper (II), copper 4-cyclohexylbutyrate (II), copper acetate (II) and copper oleate (II)

Manganese Compounds:
    acetylacetone manganese, manganese naphthenate and manganese octylate Cobalt Compounds:
    acetylacetone cobalt and cobalt naphthenate Lithium Compounds:
    acetylacetone lithium and lithium acetate Zinc Compounds:
    acetylacetone zinc and zinc naphthenate Nickel Compounds:
    acetylacetone nickel and nickel acetate Aluminum Compounds:
    acetylacetone aluminum Calcium Compounds:
    acetylacetone calcium Iron Compounds:
    acetylacetone iron (II)

Others:
    acetylacetone chromium, sodium naphthenate and rare earth octoate

Out of the above organic metal compounds (b3), copper (II) compounds or iron (II) compounds are preferred, and acetylacetone copper (II), copper acetate (II), copper oleate (II) and acetylacetone iron (II) are particularly preferred from the viewpoint of polymerization activity.

In the present invention, when the powder material (B) is mixed with the liquid material (A), the organic metal compound (b3) is existent in the mixture in an amount of preferably 0.0001 to 0.05 part by mass, particularly preferably 0.0005 to 0.03 part by mass, most preferably 0.001 to 0.01 part by mass based on 100 parts by mass of the radically polymerizable (meth)acrylic monomer (a1) in order to develop high polymerization activity. When the amount of the organic metal compound is small, the polymerization reaction does not proceed to the fullest extent and the physical properties of the cured product tend to deteriorate. When the amount is too large, it may cause the coloration or discoloration of the cured product.

Therefore, from this point of view, the amount of the organic metal compound (b3) contained in the powder material (B) is preferably 0.0003 to 0.02 part by mass, particularly preferably 0.0005 to 0.007 part by mass based on 100 parts by mass of the non-crosslinked resin particles (b1). That is, if the amount of the organic metal compound (b3) contained in the powder material (B) is set to this range, when the liquid material (A) and the powder material (B) are mixed together to ensure that the amount of the non-crosslinked resin particles (b1) based on the radically polymerizable (meth)acrylic monomer (a1) falls within the above predetermined range, the amount of the organic metal compound (b3) contained in the mixture can be set to the above range.

4. Other Components:

In the present invention, other compounding agents except for the aforementioned components (b1) to (b3) may be added to the powder material (B). Particularly, the peroxide (Z) which will be described hereinafter is preferably blended in the powder material (B) from the viewpoint of storage stability. This peroxide (Z) will be detailed hereinafter.

As another compounding agent except for the peroxide (Z) which is blended appropriately, an inorganic filler may be blended to adjust operability for clinical practice.

Examples of the inorganic filler include quartz powders, alumina powders, glass powders, calcium carbonate, titanium oxide, dry silica and wet silica which may be used alone or in combination of two or more.

Further, a dye, a pigment and a perfume may also be used. These agents including the above inorganic filler which are blended appropriately can be used according to purpose in an amount that does not adversely affect curability and the physical properties of the cured product.

<Peroxide (Z)>

The biggest feature of the present invention is that the peroxide (Z) is blended in either one or both of the aforementioned liquid material (A) and powder material (B). That is, by using this peroxide, the significant reduction of the curing rate due to a shortage of oxygen, i.e., the excessive prolongation of the curing time when the liquid material (A) and the powder material (B) are mixed together to be cured by, for example, the brush-on technique can be avoided effectively. The control of the curing time (the prolongation of the curing time) by using the aforementioned radical chain transfer agent (a3) is almost the same in both of the brush-on technique and the kneading technique. As a result, the powder-liquid curable material kit of the present invention can be advantageously used for both of the kneading technique and the brush-on technique.

That is, in the present invention, it is believed that the marked prolongation of the curing time in the brush-on technique can be avoided as described above since the peroxide (Z) serves not as a radical polymerization initiator but as an oxygen supply source especially in the brush-on technique.

Examples of the peroxide (Z) include peroxides classified into ketone peroxides, peroxyketals, hydroperoxides, diaryl peroxides, peroxy esters, diacyl peroxides and peroxydicarbonates. Specific examples of these are given below.

(Ketone Peroxides)
    methyl ethyl ketone peroxide, cyclohexanone peroxide, methyl cyclohexanone peroxide, methyl acetoacetate peroxide and acetylacetone peroxide.

(Peroxyketals)
    1,1-bis(t-hexylperoxy) 3,3,5-trimethylcyclohexane, 1,1-bis(t-hexylperoxy)cyclohexane, 1,1-bis(t-butylperoxy) 3,3,5-trimethylcyclohexane, 1,1-bis(t-butylperoxy)cyclohexane, 1,1-bis(t-butylperoxy)cyclododecane, 2,2-bis(t-butylperoxy)butane, n-butyl 4,4-bis(t-butylperoxy)valerate and 2,2-bis(4,4-di-t-butylperoxycyclohexyl)propane.

(Hydroperoxides)
    p-menthane hydroperoxide, diisopropyl benzene hydroperoxide, 1,1,3,3-tetramethylbutyl hydroperoxide, cumene hydroperoxide, t-hexyl hydroperoxide and t-butyl hydroperoxide.

(Diaryl Peroxides)
    α,α-bis(t-butylperoxy)diisopropyl benzene, dicumyl peroxide, 2,5-dimethyl-2,5-bis(t-butylperoxy)hexane, t-butylcumyl peroxide, di-t-butyl peroxide and 2,5-dimethyl-2,5-bis(t-butylperoxy)hexyne-3.

(Diacyl Peroxides)
    isobutyryl peroxide, 2,4-dichlorobenzoyl peroxide, 3,5,5-trimethylhexanoyl peroxide, octanoyl peroxide, lauroyl peroxide, stearyl peroxide, succinic acid peroxide, m-toluoylbenzoyl peroxide and benzoyl peroxide.

(Peroxydicarbonates)
  di-n-propyl peroxydicarbonate, diisopropyl peroxydicarbonate, bis(4-t-butylcyclohexyl)peroxydicarbonate, di-2-ethoxyethyl peroxydicarbonate, di-2-ethylhexyl peroxydicarbonate, di-2-methoxybutyl peroxydicarbonate and di(3-methyl-3-methoxybutyl)peroxydicarbonate.
(Peroxy Esters)
  α,α-bis(neodecanoylperoxy)diisopropyl benzene, cumyl peroxyneodecanoate, 1,1,3,3-tetramethylbutyl peroxyneodecanoate, 1-cyclohexyl-1-methylethyl peroxyneodecanoate, t-hexyl peroxyneodecanoate, t-butyl peroxyneodecanoate, t-hexyl peroxypivalate, t-butyl peroxypivalate, 1,1,3,3-tetramethylbutyl peroxy-2-ethylhexanoate, 2,5-dimethyl-2,5-bis(2-ethylhexanoylperoxy)hexane, 1-cyclohexyl-1-methylethyl peroxy-2-ethylhexanoate, t-hexyl peroxy 2-ethylhexanoate, t-butyl peroxy 2-ethylhexanoate, t-butyl peroxy isobutyrate, t-hexyl peroxy isopropyl monocarbonate, t-butylperoxymaleic acid, t-butyl peroxy 3,5,5-trimethyl hexanoate, t-butyl peroxy laurate, 2,5-dimethyl-2,5-bis(m-toluoylperoxy)hexane, t-butyl peroxy isopropyl monocarbonate, t-butyl peroxy 2-ethylhexyl monocarbonate, t-hexyl peroxy benzoate, 2,5-dimethyl-2,5-bis(benzoylperoxy)hexane, t-butyl peroxyacetate, t-butyl peroxy-m-toluoyl benzoate, t-butyl peroxy benzoate and bis(t-butylperoxy)isophthalate The aforementioned peroxides (Z) may be used alone or in combination of two or more. Out of these, peroxides having a 10-hour half-life period temperature of 60° C. or higher are desirably used from the viewpoint of storage stability.

Further, although this peroxide (Z) may be blended in either one of the liquid material (A) and the powder material (B) as described above, in general, a liquid peroxide (Z) is blended in the liquid material (A) and a solid peroxide (Z) is blended in the powder material (B). Especially in the present invention, diacyl peroxides are preferred from the viewpoint of storage stability, and solid peroxides such as benzoyl peroxide are most preferably blended in the powder material (B).

In the present invention, when the powder material (B) is mixed with the liquid material (A), the above peroxide (Z) is existent in the mixture in an amount of preferably 0.01 to 10 parts by mass, particularly preferably 0.05 to 7 parts by mass, most preferably 0.07 to 5 parts by mass based on 100 parts by mass of the radically polymerizable (meth)acrylic monomer (a1). When the amount of this peroxide is small, the effect of suppressing the excessive prolongation of the curing time when the brush-on technique is employed may become unsatisfactory. When the peroxide (Z) is used more than required, storage stability tends to deteriorate.

Therefore, whether the peroxide (Z) is blended in the liquid material (A) or the powder material (B), the amount of the peroxide (Z) based on the polymerizable monomer (a1) is set to the above range when the powder material (B) is mixed with the liquid material (A).

That is, to blend the peroxide (Z) into the liquid material (A), the above amount can be applied as it is.

To blend the peroxide (Z) into the powder material (B), the amount of the peroxide (Z) must be set in consideration of the mixing ratio of the liquid material (A) and the powder material (B). For example, the amount of the peroxide (Z) contained in the powder material (B) is preferably 0.03 to 5 parts by mass, particularly preferably 0.05 to 3 parts by mass based on 100 parts by mass of the non-crosslinked resin particles (b1). That is, if the amount of the peroxide (Z) contained in the powder material (B) is set to this range, when the liquid material (A) and the powder material (B) are mixed together to ensure that the amount of the non-crosslinked resin particles (b1) based on the radically polymerizable (meth)acrylic monomer (a1) falls within the above predetermined range, the amount of the peroxide (Z) contained in the mixture can be set to the above range.

As a matter of course, even when the peroxide is divided and blended into the liquid material (A) and the powder material (B), the amount of the peroxide (Z) contained in the liquid material (A) and the powder material (B) may be determined in consideration of the mixing ratio of the liquid material (A) and the powder material (B).

Although a combination of a peroxide and an organic metal compound is also known as a chemical polymerization initiator, the peroxide is used to supply oxygen in the present invention. That is, although a combination of a peroxide and an organic metal compound is existent in the present invention, this combination does not function as a chemical initiator.

Stated more specifically, reactivity between the peroxide and the organic metal compound which are used in combination in the present invention is very low. When a component which has high reactivity with the peroxide is existent in the present invention, the amount of the peroxide is set to a small value that is satisfactory as an oxygen supply source but not as a radical supply source which can cause polymerization. That is, the pyrimidinetrione-based polymerization initiator system employed in the present invention has an advantage that the amount of heat generated during curing is small, and when the peroxide is a radical supply source and used in an amount that can cause polymerization, the amount of heat generated during curing becomes large with the result that it is difficult to apply the powder-liquid mixture to the oral cavity. Therefore, in the present invention, the amount of the peroxide is set so small that it does not serve as a radical polymerization initiator in consideration of the mixing ratio of the liquid material (A) and the powder material (B) used for clinical practice.

For example, in the powder-liquid curable material of the present invention, extremely wide variety of components are contained in the liquid material (A) and the powder material (B), and various additives known per se are further blended into these materials. According to the circumstances, a combination which tends to produce a radical from the peroxide (Z) may be employed. Then, even in this case, heat generation during curing is checked in advance through laboratory experiments so as to limit the amount of the peroxide (Z) so that heat generation is suppressed to such an extent that it does not place a burden on a patient. In general, the amount of the peroxide (Z) should be set to less than 0.5 part by mass, particularly 0.1 to 0.2 part by mass based on 100 parts by mass of the mixture of the liquid material (A) and the powder material (B).

<Powder-Liquid Curable Material Kit>

The aforementioned liquid material (A) and powder material (B) are prepared by uniformly mixing together predetermined amounts of components, stored in separate containers in such a manner that they do not contact each other and used for dental purposes as a powder-liquid curable material kit like a conventionally known one.

That is, this powder-liquid curable material kit can be used as a shared kit which can be used for both of the kneading technique and the brush-on technique. In both of the techniques, the liquid material (A) and the powder material (B) are mixed together and the resulting mixture (curable material) is applied to a predetermined site to carry out polymerization curing so as to form a cured product.

Whether the liquid material (A) and the powder material (B) are mixed together by any one of the techniques, the mixing ratio is set such that the amount of the non-cross-linked resin particles (b1) contained in the powder material (B) becomes 30 to 400 parts by mass (particularly 100 to 300 parts by mass) based on 100 parts by mass of the polymerizable monomer (a1) contained in the liquid material (A) as described above.

In general, the mixing ratio of the powder material (g) to the liquid material (ml) is 0.3/1 to 4/1. For clinical practice, in many cases, the mixing ratio of the powder material (g) to the liquid material (ml) is 2/1.

In the powder-liquid curable material kit of the present invention, when the curable material (a mixture of the liquid material and the powder material) is prepared by employing the kneading technique to be cured, the time (curing time) from the mixing of the powder material (A) and the liquid material (B) to the completion of curing is 1 minute 30 seconds to 3 minutes, particularly 1 minute 40 seconds to 2 minutes 20 seconds. Meanwhile, when the brush-on technique is employed, the curing time from the compatibilization of the liquid material (A) oozing out from the absorbing material 3 of FIG. 1 with the powder material (B) to the completion of curing is 3 to 4 minutes, particularly 3 minutes 10 seconds to 3 minutes 40 seconds. In both of these techniques, a curable material having high operability can be obtained.

EXAMPLES

The following examples are provided for the purpose of further illustrating the present invention but are in no way to be taken as limiting.

The abbreviations of compounds and measurement methods used in examples and comparative examples are as follows.
radically polymerizable (meth)acrylic monomer (a1);
    MMA: methyl methacrylate
    TMPT: trimethylolpropane trimethacrylate
Organic halogen compound (a2);
    DLDMACl: dilauryl dimethyl ammonium chloride
    DLDMABr: dilauryl dimethyl ammonium bromide
Radical chain transfer agent (a3);
    α-MSD: 2,4-diphenyl-4-methyl-1-pentene
Non-crosslinked resin particles (b1);
    PEMA: ethyl polymethacrylate
    P(MMA-EMA): methyl methacrylate-ethyl methacrylate copolymer
Pyrimidinetrione compound (b2);
    cHexEt-PTO: 1-cyclohexyl-5-ethyl pyrimidinetrione
    cHexMe-PTO: 1-cyclohexyl-5-methyl pyrimidinetrione
organic metal compound (b3);
    CuAcAc: acetylacetone copper
    CuAc: cupric acetate
peroxide (Z);
    BPO: benzoyl peroxide
    peroctaH: 1,1,3,3-tetramethylbutyl hydroperoxide
polymerization inhibitor;
    BHT: butyl hydroxytoluene (1-1) Measurement of Curing Time (Brush-on Technique);

The powder material (B) and the liquid material (A) were put into separate containers, and an absorbing material (writing brush) was impregnated with the liquid material. This absorbing material was applied to the powder material (B) to compatibilize the liquid material (A) oozing out from the absorbing material with the powder material (B) so as to prepare resin sludge (curable material).

The resin sludge was touched by hand to check whether a fingernail mark was left thereon. The time from the application of the absorbing material containing the liquid material (A) to the powder material (B) until no fingernail mark was left any more was measured and taken as a curing time in the brush-on technique. The measurement was made in a 23° C. constant temperature room.

The resin sludge was prepared by mixing together the powder material (g) and the liquid material (ml) in a ratio of 2/1.

The curing time in the brush-on technique is most preferably 3 to 4 minutes from the viewpoint of operability. When the curing time is longer than 4 minutes, it is difficult to use the kit for a case where curing in the oral cavity is desired at the time of controlling the TEK inner wall.

(1-2) Measurement of Curing Time (Kneading Technique);

The powder material (B) and the liquid material (A) were put into a rubber cup in a powder material (g)/liquid material (ml) ratio of 2/1 and kneaded together for 20 seconds. The resulting kneaded product was taken out from the rubber cup and touched by hand to check whether a fingernail mark was left thereon. The time from the start of kneading until no fingernail mark was left any more was measured and taken as a curing time in the kneading technique. The measurement was made in a 23° C. constant temperature room.

The curing time in the kneading technique is most preferably 1 minute 30 seconds to 3 minutes since quick curing is desired right after form adjustment.

(2) Measurement of Curing Heat Generation

The evaluation of curing heat generation was carried out by a heat generation method using a thermistor thermometer.

The powder material (B) and the liquid material (A) were mixed together in a B/A ratio of 2/1 (g/ml) and kneaded together for 20 seconds. Then, the resulting mixture was poured into a Teflon mold (30 mm×30 mm×12 mm) having a 9 mm-diameter hole at the center, and the thermistor thermometer was inserted into the mixture to measure the maximum temperature with a recorder. The measurement was made in a 23° C. constant temperature room.

Since a normal-temperature dental polymerization resin is often cured in the oral cavity of a patient, the maximum temperature of curing heat generation is preferably lower than 60° C. and when the temperature exceeds 60° C., it hurts a patient.

(3) Measurement of Flexural Strength;

The flexural strength of the cured product was measured by the following method.

The powder material (B) and the liquid material (A) were mixed together in a B/A ratio of 2/1 (g/ml) and kneaded together for 20 seconds. Then, the resulting mixture was poured into a 25 mm×2 mm×2 mm mold and cured at 37° C. for 24 hours. A bending fracture test was made on the cured product obtained as described above at a distance between fulcrums of 20 mm. The cross head speed was 1 mm/min. The measurement was made in a 23° C. constant temperature room.

(4) Color Test of Cured Product;

The color test of the cured product was carried out by the following method. First of all, the powder material (g) and the liquid material (ml) were mixed together in a ratio of 2/1 and kneaded together for 20 seconds. Then, the resulting mixture was poured into a 10 mm×10 mm×1 mm mold and cured at 37° C. for 24 hours. The color of the cured product obtained as described above was evaluated visually.

Example 1

The following components were stirred and mixed together for 3 hours according to the following formulation to obtain the liquid material (A).

| Polymerizable monomer (a1); | |
| --- | --- |
| Methyl methacrylate | 90 g |
| Trimethylolpropane trimethacrylate | 10 g |
| Organic halogen compound (a2); | |
| Dilauryl dimethyl ammonium chloride | 0.2 g |
| Radical chain transfer agent (a3); | |
| 2,4-diphenyl-4-methyl-1-pentene | 0.2 g |
| Polymerization inhibitor (other); | |
| Butyl hydroxytoluene | 0.1 g |

Meanwhile, the following components were mixed together by using a rocking mixture for 3 hours according to the following formulation to obtain the powder material (B).

| Non-crosslinked resin particles (b1); | |
| --- | --- |
| Ethyl polymethacrylate (average particle diameter of 35 μm) | 10 g |
| Methyl methacrylate-ethyl methacrylate copolymer (average particle diameter of 60 μm) | 90 g |
| Pyrimidinetrione compound (b2); | |
| 1-cyclohexyl-5-ethyl pyrimidinetrione | 1.5 g |

| Organic metal compound (b3); | |
| --- | --- |
| Acetylacetone copper | 0.002 g |
| Peroxide (Z); | |
| Benzoyl peroxide | 0.15 g |

The curing time, curing heat generation, flexural strength and the color of the cured product when the brush-on technique and the kneading technique were employed were evaluated by using the obtained normal-temperature polymerization powder-liquid curable material kit composed of the powder material (B) and the liquid material (A).

The compositions of the liquid material (A) and the powder material (B) in the curable material kit are shown in Table 1, and the test results are shown in Table 3.

Examples 2 to 39

Powder-liquid curable material kits were prepared in the same manner as in Example 1 except that the formulations (compositions) of the liquid material (A) and the powder material (B) were changed as shown in Table 1 or Table 2 to evaluate the curing time, curing heat generation, flexural strength and the color of the cured product. The test results are shown in Table 3.

Comparative Examples 1 to 17

Powder-liquid curable material kits were prepared in the same manner as in Example 1 except that the formulations (compositions) of the liquid material (A) and the powder material (B) were changed as shown in Table 4 to evaluate the curing time, curing heat generation, flexural strength and the color of the cured product. The test results are shown in Table 5.

TABLE 1

| | Composition of curable material kit/parts by mass | | | | | | | | | |
| --- | --- | --- | --- | --- | --- | --- | --- | --- | --- | --- |
| | (a1) | | (a2) | (a3) | Other | (z) | (b1) | | (b2) | (b3) |
| | Liquid Material (A) | | | | | | Powder Material (B) | | | |
| | MMA | TMPT | *1 *2 | α-MSD | BHT | BPO | PEMA | *3 | *4 *5 | CuAcAc | CuAc |
| Ex. 1 | 90 | 10 | 0.2 | 0.2 | 0.1 | 0.15 | 10 | 90 | 1.5 | 0.002 | |
| Ex. 2 | 90 | 10 | 0.2 | 0.2 | 0.1 | 0.15 | 10 | 90 | 1.5 | 0.002 | |
| Ex. 3 | 90 | 10 | 0.2 | 0.2 | 0.1 | 0.15 | 10 | 90 | 0.05 | 0.002 | |
| Ex. 4 | 90 | 10 | 0.2 | 0.2 | 0.1 | 0.15 | 10 | 90 | 2.5 | 0.002 | |
| Ex. 5 | 90 | 10 | 0.2 | 0.2 | 0.1 | 0.15 | 10 | 90 | 0.04 | 0.002 | |
| Ex. 6 | 90 | 10 | 0.2 | 0.2 | 0.1 | 0.15 | 10 | 90 | 4 | 0.002 | |
| Ex. 7 | 90 | 10 | 0.2 | 0.2 | 0.1 | 0.15 | 10 | 90 | 0.03 | 0.002 | |
| Ex. 8 | 90 | 10 | 0.2 | 0.2 | 0.1 | 0.15 | 10 | 90 | 5 | 0.002 | |
| Ex. 9 | 90 | 10 | 0.2 | 0.2 | 0.1 | 0.15 | 10 | 90 | 1.5 | | 0.002 |
| Ex. 10 | 90 | 10 | 0.2 | 0.2 | 0.1 | 0.15 | 10 | 90 | 1.5 | 0.0005 | |
| Ex. 11 | 90 | 10 | 0.2 | 0.2 | 0.1 | 0.15 | 10 | 90 | 1.5 | 0.005 | |
| Ex. 12 | 90 | 10 | 0.2 | 0.2 | 0.1 | 0.15 | 10 | 90 | 1.5 | 0.0004 | |
| Ex. 13 | 90 | 10 | 0.2 | 0.2 | 0.1 | 0.15 | 10 | 90 | 1.5 | 0.014 | |
| Ex. 14 | 90 | 10 | 0.2 | 0.2 | 0.1 | 0.15 | 10 | 90 | 1.5 | 0.0003 | |
| Ex. 15 | 90 | 10 | 0.2 | 0.2 | 0.1 | 0.15 | 10 | 90 | 1.5 | 0.02 | |
| Ex. 16 | 90 | 10 | 0.2 | 0.2 | 0.1 | 0.15 | 10 | 90 | 1.5 | 0.002 | |
| Ex. 17 | 90 | 10 | 0.01 | 0.2 | 0.1 | 0.15 | 10 | 90 | 1.5 | 0.002 | |
| Ex. 18 | 90 | 10 | 2 | 0.2 | 0.1 | 0.15 | 10 | 90 | 1.5 | 0.002 | |
| Ex. 19 | 90 | 10 | 0.001 | 0.2 | 0.1 | 0.15 | 10 | 90 | 1.5 | 0.002 | |
| Ex. 20 | 90 | 10 | 5 | 0.2 | 0.1 | 0.15 | 10 | 90 | 1.5 | 0.002 | |

*1: DLDMACl,
*2: DLDMABr,
*3: P(MMA-EMA),
*4: cHexEt-PTO,
*5: cHexMe-PTO

TABLE 2

| | Composition of curable material kit/parts by mass | | | | | | | | | | |
|---|---|---|---|---|---|---|---|---|---|---|---|
| | (a1) | (a2) | (a3) | Other | (Z) | | (b1) | (b2) | | | (b3) |
| | Liquid Material (A) | | | | | | Powder Material (B) | | | | |
| | MMA | TMPT | DLDMACl | α-MSD | BHT | peroctaH | BPO | PEMA | P (MMA-EMA) | cHexEt-PTO | CuAcAc |
| Ex. 21 | 90 | 10 | 0.2 | 0.05 | 0.1 | | 0.15 | 10 | 90 | 1.5 | 0.002 |
| Ex. 22 | 90 | 10 | 0.2 | 5 | 0.1 | | 0.15 | 10 | 90 | 1.5 | 0.002 |
| Ex. 23 | 90 | 10 | 0.2 | 0.03 | 0.1 | | 0.15 | 10 | 90 | 1.5 | 0.002 |
| Ex. 24 | 90 | 10 | 0.2 | 7 | 0.1 | | 0.15 | 10 | 90 | 1.5 | 0.002 |
| Ex. 25 | 90 | 10 | 0.2 | 0.01 | 0.1 | | 0.15 | 10 | 90 | 1.5 | 0.002 |
| Ex. 26 | 90 | 10 | 0.2 | 10 | 0.1 | | 0.15 | 10 | 90 | 1.5 | 0.002 |
| Ex. 27 | 90 | 10 | 0.2 | 0.2 | 0.1 | 0.3 | | 10 | 90 | 1.5 | 0.002 |
| Ex. 28 | 90 | 10 | 0.2 | 0.2 | 0.1 | 0.15 | 0.075 | 10 | 90 | 1.5 | 0.002 |
| Ex. 29 | 90 | 10 | 0.2 | 0.2 | 0.1 | | 0.05 | 10 | 90 | 1.5 | 0.002 |
| Ex. 30 | 90 | 10 | 0.2 | 0.2 | 0.1 | | 2.5 | 10 | 90 | 1.5 | 0.002 |
| Ex. 31 | 90 | 10 | 0.2 | 0.2 | 0.1 | | 0.04 | 10 | 90 | 1.5 | 0.002 |
| Ex. 32 | 90 | 10 | 0.2 | 0.2 | 0.1 | | 4 | 10 | 90 | 1.5 | 0.002 |
| Ex. 33 | 90 | 10 | 0.2 | 0.2 | 0.1 | | 0.03 | 10 | 90 | 1.5 | 0.002 |
| Ex. 34 | 90 | 10 | 0.2 | 0.2 | 0.1 | | 5 | 10 | 90 | 1.5 | 0.002 |
| Ex. 35 | 100 | | 0.2 | 0.2 | 0.1 | | 0.15 | 10 | 90 | 1.5 | 0.002 |
| Ex. 36 | 80 | 20 | 0.2 | 0.2 | 0.1 | | 0.15 | 10 | 90 | 1.5 | 0.002 |
| Ex. 37 | 90 | 10 | 0.2 | 0.2 | 0.1 | | 0.15 | | 100 | 1.5 | 0.002 |
| Ex. 38 | 90 | 10 | 0.2 | 0.2 | 0.1 | | 0.15 | 20 | 80 | 1.5 | 0.002 |
| Ex. 39 | 90 | 10 | 0.2 | 0.2 | | | 0.15 | 10 | 90 | 1.5 | 0.002 |

TABLE 3

| | Results | | | | |
|---|---|---|---|---|---|
| | Curing time | | Curing heat generation (° C.) | Flexural strength (MPa/cm²) | Color |
| | Brush-on technique | Kneading technique | | | |
| Ex. 1 | 3 min 20 sec | 1 min 50 sec | 51 | 75 | Clear and colorless |
| Ex. 2 | 3 min 25 sec | 1 min 55 sec | 52 | 73 | Clear and colorless |
| Ex. 3 | 3 min 30 sec | 2 min | 50 | 72 | Clear and colorless |
| Ex. 4 | 3 min 25 sec | 1 min 55 sec | 52 | 73 | Clear and colorless |
| Ex. 5 | 3 min 35 sec | 2 min 10 sec | 49 | 70 | Clear and colorless |
| Ex. 6 | 3 min 20 sec | 1 min 55 sec | 53 | 71 | Clear and colorless |
| Ex. 7 | 3 min 40 sec | 2 min 20 sec | 49 | 66 | Clear and colorless |
| Ex. 8 | 3 min 25 sec | 1 min 50 sec | 52 | 67 | Clear and colorless |
| Ex. 9 | 3 min 30 sec | 1 min 55 sec | 51 | 76 | Clear and colorless |
| Ex. 10 | 3 min 30 sec | 2 min | 50 | 73 | Clear and colorless |
| Ex. 11 | 3 min 20 sec | 1 min 50 sec | 52 | 74 | Clear and colorless |
| Ex. 12 | 3 min 35 sec | 2 min 5 sec | 50 | 71 | Clear and colorless |
| Ex. 13 | 3 min 25 sec | 1 min 55 sec | 53 | 73 | Clear and colorless |
| Ex. 14 | 3 min 40 sec | 2 min 15 sec | 49 | 65 | Clear and colorless |
| Ex. 15 | 3 min 20 sec | 1 min 50 sec | 53 | 72 | Very light blue |
| Ex. 16 | 3 min 30 sec | 1 min 55 sec | 53 | 70 | Clear and colorless |
| Ex. 17 | 3 min 35 sec | 2 min 5 sec | 50 | 71 | Clear and colorless |
| Ex. 18 | 3 min 25 sec | 1 min 50 sec | 52 | 73 | Clear and colorless |
| Ex. 19 | 3 min 40 sec | 2 min 10 sec | 48 | 66 | Clear and colorless |
| Ex. 20 | 3 min 25 sec | 1 min 50 sec | 53 | 73 | Very light yellow |
| Ex. 21 | 3 min 10 sec | 1 min 40 sec | 52 | 74 | Clear and colorless |
| Ex. 22 | 3 min 30 sec | 2 min | 50 | 73 | Clear and colorless |
| Ex. 23 | 3 min 5 sec | 1 min 35 sec | 55 | 74 | Clear and colorless |
| Ex. 24 | 3 min 40 sec | 2 min 10 sec | 48 | 71 | Clear and colorless |
| Ex. 25 | 3 min | 1 min 30 sec | 58 | 75 | Clear and colorless |
| Ex. 26 | 3 min 50 sec | 2 min 25 sec | 47 | 65 | Clear and colorless |
| Ex. 27 | 3 min 30 sec | 1 min 50 sec | 50 | 75 | Clear and colorless |
| Ex. 28 | 3 min 25 sec | 1 min 55 sec | 52 | 73 | Clear and colorless |
| Ex. 29 | 3 min 25 sec | 1 min 50 sec | 51 | 74 | Clear and colorless |
| Ex. 30 | 3 min 20 sec | 1 min 50 sec | 50 | 75 | Clear and colorless |
| Ex. 31 | 3 min 35 sec | 1 min 55 sec | 52 | 71 | Clear and colorless |
| Ex. 32 | 3 min 25 sec | 1 min 50 sec | 52 | 72 | Clear and colorless |
| Ex. 33 | 3 min 50 sec | 1 min 55 sec | 50 | 72 | Clear and colorless |
| Ex. 34 | 3 min 20 sec | 1 min 55 sec | 51 | 71 | Clear and colorless |
| Ex. 35 | 3 min 20 sec | 1 min 55 sec | 52 | 75 | Clear and colorless |
| Ex. 36 | 3 min 20 sec | 1 min 50 sec | 51 | 76 | Clear and colorless |
| Ex. 37 | 3 min 25 sec | 1 min 50 sec | 52 | 74 | Clear and colorless |
| Ex. 38 | 3 min 20 sec | 1 min 50 sec | 51 | 75 | Clear and colorless |
| Ex. 39 | 3 min 15 sec | 1 min 45 sec | 51 | 76 | Clear and colorless |

TABLE 4

| | Composition of curable material kit/parts by mass | | | | | | | | | |
|---|---|---|---|---|---|---|---|---|---|---|
| | (a1) | (a2) | (a3) | Other | (Z) | | (b1) | | (b2) | (b3) |
| | | Material (A) | | | | | Material (B) | | | |
| | MMA | TMPT | DLDMACl | α-MSD | BHT | BPO | PEMA | P(MMA-EMA) | cHexEt-PTO | CuAcAc |
| Comp. Ex. 1 | 90 | 10 | 0.2 | 0.2 | 0.1 | | 10 | 90 | 1.5 | 0.002 |
| Comp. Ex. 2 | 90 | 10 | 0.2 | 0.2 | 0.1 | | 10 | 90 | 2.5 | 0.002 |
| Comp. Ex. 3 | 90 | 10 | 0.2 | 0.2 | 0.1 | | 10 | 90 | 1.5 | 0.005 |
| Comp. Ex. 4 | 90 | 10 | 2 | 0.2 | 0.1 | | 10 | 90 | 1.5 | 0.002 |
| Comp. Ex. 5 | 90 | 10 | 0.2 | 0.05 | 0.1 | | 10 | 90 | 1.5 | 0.002 |
| Comp. Ex. 6 | 80 | 20 | 0.2 | 0.2 | 0.1 | | 10 | 90 | 1.5 | 0.002 |
| Comp. Ex. 7 | 90 | 10 | 0.2 | 0.2 | 0.1 | | 10 | 90 | 7 | 0.002 |
| Comp. Ex. 8 | 90 | 10 | 0.2 | 0.2 | 0.1 | | 10 | 90 | 1.5 | 0.04 |
| Comp. Ex. 9 | 90 | 10 | 7 | 0.2 | 0.1 | | 10 | 90 | 1.5 | 0.002 |
| Comp. Ex. 10 | 90 | 10 | 0.2 | 0.2 | 0.1 | | 10 | 90 | 7 | 0.04 |
| Comp. Ex. 11 | 90 | 10 | 7 | 0.2 | 0.1 | | 10 | 90 | 7 | 0.002 |
| Comp. Ex. 12 | 90 | 10 | 7 | 0.2 | 0.1 | | 10 | 90 | 1.5 | 0.04 |
| Comp. Ex. 13 | 90 | 10 | 7 | 0.2 | 0.1 | | 10 | 90 | 7 | 0.04 |
| Comp. Ex. 14 | 90 | 10 | 0.2 | 0.2 | 0.1 | 0.15 | 10 | 90 | | 0.002 |
| Comp. Ex. 15 | 90 | 10 | 0.2 | 0.2 | 0.1 | 0.15 | 10 | 90 | 1.5 | |
| Comp. Ex. 16 | 90 | 10 | | 0.2 | 0.1 | 0.15 | 10 | 90 | 1.5 | 0.002 |
| Comp. Ex. 17 | 90 | 10 | 0.2 | | 0.1 | 0.15 | 10 | 90 | 1.5 | 0.002 |

TABLE 5

| | Results | | | | |
|---|---|---|---|---|---|
| | Curing time | | Curing heat | Flexural | |
| | Brush-on technique | Kneading technique | generation (° C.) | strength (MPa/cm²) | Color |
| Comp. Ex. 1 | 5 min 30 sec | 1 min 50 sec | 50 | 73 | Clear and colorless |
| Comp. Ex. 2 | 5 min 35 sec | 1 min 55 sec | 50 | 71 | Clear and colorless |
| Comp. Ex. 3 | 5 min 30 sec | 1 min 55 sec | 50 | 72 | Clear and colorless |
| Comp. Ex. 4 | 5 min 30 sec | 1 min 50 sec | 51 | 72 | Clear and colorless |
| Comp. Ex. 5 | 5 min 10 sec | 1 min 35 sec | 56 | 73 | Clear and colorless |
| Comp. Ex. 6 | 5 min 30 sec | 1 min 50 sec | 52 | 73 | Clear and colorless |
| Comp. Ex. 7 | 5 min 40 sec | 1 min 55 sec | 52 | 67 | Clear and colorless |
| Comp. Ex. 8 | 5 min 35 sec | 1 min 55 sec | 52 | 73 | Light blue |
| Comp. Ex. 9 | 5 min 30 sec | 1 min 55 sec | 51 | 72 | Light yellow |
| Comp. Ex. 10 | 5 min 15 sec | 1 min 35 sec | 52 | 70 | Light blue |
| Comp. Ex. 11 | 5 min 10 sec | 1 min 30 sec | 51 | 71 | Light yellow |
| Comp. Ex. 12 | 5 min 15 sec | 1 min 30 sec | 50 | 73 | Light yellow |
| Comp. Ex. 13 | 5 min 5 sec | 1 min 20 sec | 52 | 73 | Light yellow |
| Comp. Ex. 14 | — | — | — | — | — |
| Comp. Ex. 15 | — | — | — | — | — |
| Comp. Ex. 16 | — | — | — | — | — |
| Comp. Ex. 17 | 2 min 40 sec | 1 min | 73 | 75 | Clear and colorless |

In Examples 1 to 39 of the present invention, the curing time in both of the brush-on technique and the kneading technique fell within the optimum range. The amount of generated heat was satisfactory due to the blending of 2,4-diphenyl-4-methyl-1-pentene which is a radical chain transfer agent.

Meanwhile, in Comparative Examples 1 to 13 in which no peroxide (Z) was used, although the curing time in the kneading technique fell within the optimum range, the curing time in the brush-on technique was very long.

In Comparative Examples 14 to 16 in which the pyrimidinetrione compound (b2), the organic metal compound (b3) or the organic halogen compound (b3) was not used, the resulting mixture was not cured and a curable material (normal-temperature polymerization resin) could not be prepared.

In Comparative Example 17 in which no radical chain transfer agent (a3) was used, in both of the brush-on technique and the kneading technique, the curing time was much shorter than those of Examples with the result that an enough operation time could not be taken and it was difficult to use the obtained kit. Curing heat generation was high and would hurt a patient.

The invention claimed is:

1. A powder-liquid dental curable material kit composed of a liquid material (A) and a powder material (B) and including a combination of an organic halogen compound, a pyrimidinetrione compound and an organic metal compound as a radical polymerization initiator, wherein
   the liquid material (A) contains a radically polymerizable (meth)acrylic monomer (a1), the organic halogen compound (a2) and a radical chain transfer agent (a3); the powder material (B) contains (b1) non-crosslinked resin particles, (b2) the pyrimidinetrione compound and (b3) the organic metal compound; and (Z) a peroxide is contained in at least one of the liquid material (A) and the powder material (B), the peroxide serving as an oxygen source, and being contained in an amount of less than 0.5 parts by mass per 100 parts by mass of the sum of the liquid material (A) and the powder material (B).

2. The powder-liquid dental curable material kit according to claim 1, wherein the liquid material (A) contains 0.001 to 5 parts by mass of the organic halogen compound (a2) and 0.01 to 10 parts by mass of the radical chain transfer agent (a3) based on 100 parts by mass of the radically polymerizable monomer (a1); and the powder material (B) contains 0.03 to 5 parts by mass of the pyrimidinetrione compound (b2) and 0.0003 to 0.02 part by mass of the organic metal compound (b3) based on 100 parts by mass of the resin particles (b1).

3. The powder-liquid dental curable material kit according to claim 2, wherein the peroxide (Z) is blended in the powder material (B) in an amount of 0.03 to 5 parts by mass based on 100 parts by mass of the resin particles (b1).

4. The powder-liquid dental curable material kit according to claim 1, wherein the organic halogen compound (a2) is a quaternary ammonium halide.

5. The powder-liquid dental curable material kit according to claim 1, wherein the radical chain transfer agent (a3) is a mercaptan, halogenated hydrocarbon or phenyl group-containing mono-olefin.

6. The powder-liquid dental curable material kit according to claim 1, wherein the non-crosslinked resin particles (b1) are (meth)acrylate resin particles.

7. The powder-liquid dental curable material kit according to claim 1, wherein the pyrimidinetrione compound is a compound represented by the following general formula (1):

[chemical formula 1]

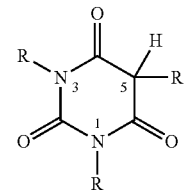

(1)

wherein three R's are each independently a hydrogen atom, alkyl group having 1 to 8 carbon atoms, cycloalkyl group having 3 to 8 carbon atoms or phenyl group, with the proviso that all of them cannot be hydrogen atoms.

8. The powder-liquid dental curable material kit according to claim 1, wherein the organic metal compound (b3) is a copper or iron compound.

9. The powder-liquid dental curable material kit according to claim 8, wherein the organic metal compound (b3) is at least one selected from the group consisting of acetylacetone copper (II), copper acetate (II), copper oleate (II) and acetylacetone iron (II).

10. A method of using the powder-liquid dental curable material kit of claim 1, comprising the step of:
    mixing together the liquid material (A) and the powder material (B) by a brush-on technique to cure the mixture.

11. The powder-liquid dental curable material kit of claim 1, wherein the powder-liquid dental curable material kit is capable of being used for both of a brush-on technique and a kneading technique.

* * * * *